US012611544B2

(12) United States Patent
    Wang

(10) Patent No.: US 12,611,544 B2
(45) Date of Patent: Apr. 28, 2026

(54) PACING CONTROL METHOD, PACING CONTROL APPARATUS, AND MEDICAL DEVICE

(71) Applicant: UNITED INNOMED (SHANGHAI) LIMITED

(72) Inventor: Li Wang, Shanghai (CN)

(73) Assignee: UNITED INNOMED (SHANGHAI) LIMITED, Shanghai (CN)

( * ) Notice: Subject to any disclaimer, the term of this patent is extended or adjusted under 35 U.S.C. 154(b) by 274 days.

(21) Appl. No.: 18/140,676

(22) Filed: Apr. 28, 2023

(65) Prior Publication Data

US 2023/0256257 A1      Aug. 17, 2023

Related U.S. Application Data

(63) Continuation-in-part of application No. PCT/CN2021/128710, filed on Nov. 4, 2021.

(30) Foreign Application Priority Data

Nov. 5, 2020    (CN) .......................... 202011222921.4

(51) Int. Cl.
    *A61N 1/39*          (2006.01)
    *A61B 5/024*         (2006.01)
                (Continued)

(52) U.S. Cl.
    CPC ...... *A61N 1/39622* (2017.08); *A61B 5/02405* (2013.01); *A61N 1/36592* (2013.01)

(58) Field of Classification Search
    CPC ................ A61N 1/3622; A61N 1/3625; A61N 1/36592; A61N 1/3621
    See application file for complete search history.

(56) References Cited

U.S. PATENT DOCUMENTS 3,999,557 A * 12/1976 Citron ................ A61N 1/37211
                                                    607/30
4,172,459 A * 10/1979 Hepp .................... A61B 5/7203
                                                    600/510
(Continued)

FOREIGN PATENT DOCUMENTS

CN          104870050 A      8/2015
CN          105999549 A      10/2016
            (Continued)

OTHER PUBLICATIONS

Jan. 28, 2022 International Search Report issued in International Patent Application No. PCT/CN2021/128710.
(Continued)

*Primary Examiner* — Brian T Gedeon

(57)                ABSTRACT

Disclosed are a pacing control method, a pacing control apparatus, and a medical device. The pacing control method comprises: obtaining an actual heart rate of a patient; and when the actual heart rate meets a preset low heart rate condition, performing cardiac pacing on the patient by using a preset pacing frequency, the preset low heart rate condition being used for representing that the patient is in a life-critical state. The method takes the patient in the life-critical state where the heart rate is severely too slow or even cardiac arrest occurs as an object needing pacing support, and achieves the effect of timely and effectively pacing to support the life of the patient and the effect of avoiding, to a great extent, unnecessary pacing for the patient and the pain of the patient caused by pacing stimulation, especially cannot trigger pacing to occasional bradycardia, non-severe bradycardia, or transient arrest.

18 Claims, 7 Drawing Sheets

(51) Int. Cl.

| | | |
|---|---|---|
| *A61N 1/362* | (2006.01) | |
| *A61N 1/365* | (2006.01) | |

(56) References Cited

U.S. PATENT DOCUMENTS

| | | | |
|---|---|---|---|
| 5,078,134 | A | 1/1992 | Heilman et al. |
| 2005/0240234 | A1 * | 10/2005 | Joo .......................... A61B 7/00 607/6 |
| 2013/0030487 | A1 | 1/2013 | Keel et al. |
| 2013/0325078 | A1 | 12/2013 | Whiting et al. |
| 2015/0335894 | A1 * | 11/2015 | Bornzin ............... A61N 1/3756 607/18 |
| 2016/0051154 | A1 | 2/2016 | Iwawaki |
| 2016/0303371 | A1 | 10/2016 | Whiting et al. |
| 2018/0256908 | A1 | 9/2018 | Casavant et al. |
| 2018/0280702 | A1 | 10/2018 | Reddy et al. |
| 2018/0361150 | A1 | 12/2018 | Ternes et al. |

FOREIGN PATENT DOCUMENTS

| | | | |
|---|---|---|---|
| CN | 106938121 | A | 7/2017 |
| CN | 110740779 | A | 1/2020 |
| JP | 2000051373 | A | 2/2000 |
| JP | 2016043041 | A | 4/2016 |
| WO | WO-2013096407 | A2 * | 6/2013 ........... A61N 1/3622 |

OTHER PUBLICATIONS

Jan. 30, 2022 Written Opinion of the International Searching Authority issued in International Patent Application No. PCT/CN2021/128710.

Jul. 2, 2023 First Office Action issued in Chinese Patent Application No. 202011222921.4.

Jul. 1, 2023 Search Report issued in Chinese Patent Application No. 202011222921.4.

Jan. 31, 2024 Second Office Action issued in Chinese Patent Application No. 202011222921.4.

Feb. 20, 2024 First Office Action issued in Japanese Patent Application No. 2023-527392.

Mar. 12, 2024 Supplementary European Search Report issued in European Patent Application No. 21888619.0.

Nov. 12, 2024 First Office Action issued in Japanese Patent Application No. 2023-527392.

Apr. 28, 2025 Third Office Action issued in Japanese Patent Application No. 2023-527392.

Jan. 20, 2026 Notice of Reasons for Refusal issued in Japanese Patent Application No. 2023-527392.

\* cited by examiner

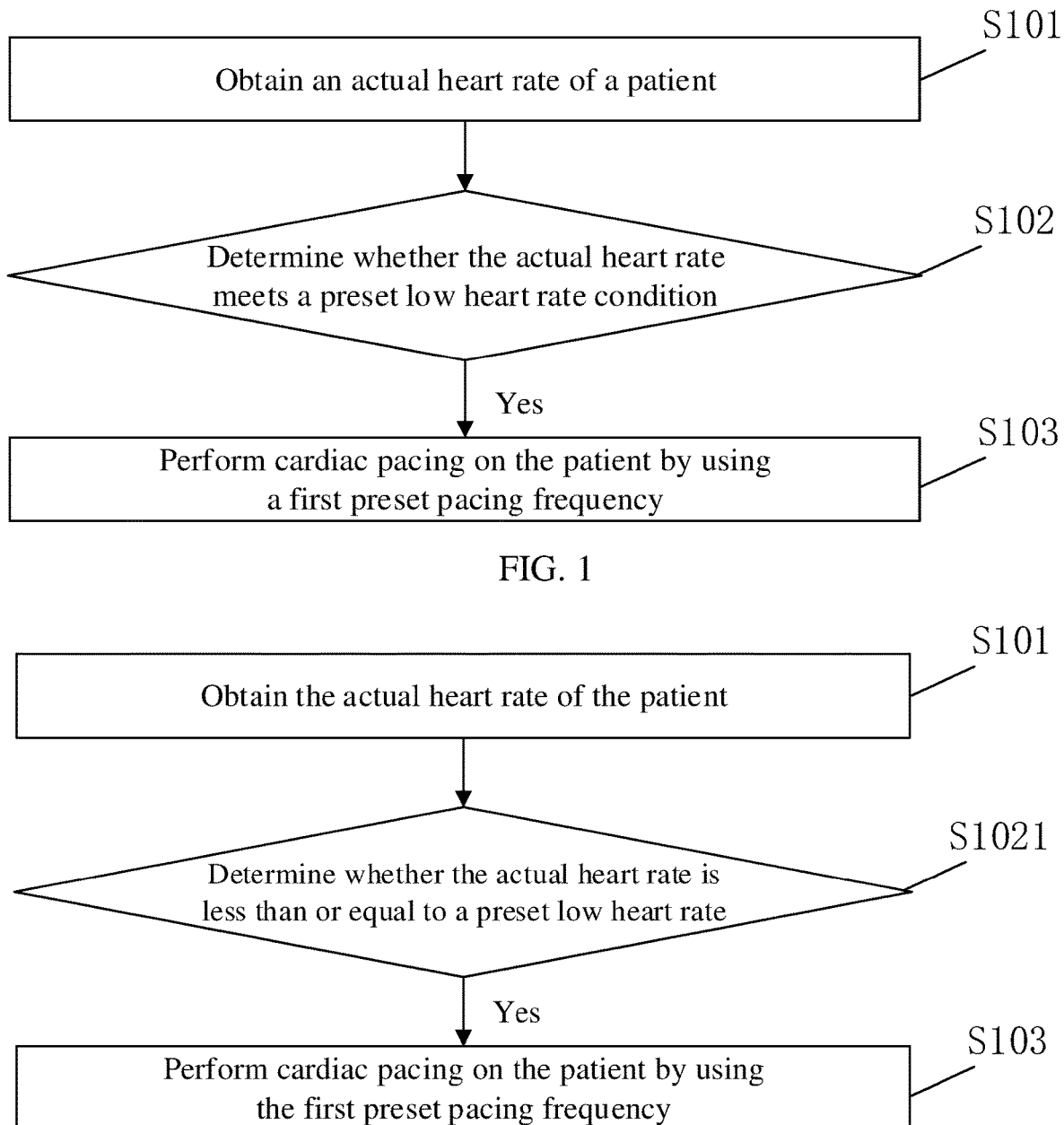

S101

Obtain an actual heart rate of a patient

S102

Determine whether the actual heart rate
meets a preset low heart rate condition

Yes

S103

Perform cardiac pacing on the patient by using
a first preset pacing frequency

Obtain the actual heart rate of the patient

S1021

Determine whether the actual heart rate is
less than or equal to a preset low heart rate Yes

S103

Perform cardiac pacing on the patient by using
the first preset pacing frequency

FIG. 2

PACING CONTROL METHOD, PACING CONTROL APPARATUS, AND MEDICAL DEVICE

CROSS-REFERENCE TO RELATED APPLICATIONS

The present application is a Continuation-In-Part Application of PCT Application No. PCT/CN2021/128710 filed on Nov. 4, 2021, which claims the priority of Chinese patent application 2020112229214 filed on Nov. 5, 2020. The contents of the above patent applications are hereby incorporated by reference herein in its entirety.

TECHNICAL FIELD

The present disclosure relates to the technical field of medical apparatus, in particular to a pacing control method, a pacing control apparatus, and a medical device.

BACKGROUND

Real-time monitoring of a patient's heart rate, and performing timely cardiac pacing when the heart rate meets a given pacing condition to avoid too slow heart rate or even asystole (cardiac arrest) is the most basic purpose of a cardiac medical device.

Existing pacing control methods are based on a preset low-limit heart rate, that is, pacing is performed on the patient at the same pacing rate as the preset low-limit heart rate once the monitored patient's heart rate decreases to the preset low-limit heart rate, so as to prevent the patient's heart rate from falling below a given value and keep the patient's heart rate not below the preset low-limit heart rate. For example, when the preset low-limit heart rate is set to 45 bpm, once the monitored patient's heart rate (one heartbeat or R-R interval) is below 45 bpm, pacing is performed on the patient by using a pacing rate of 45 bpm so that the R-R interval of the patient's heart rate will be no longer than the R-R interval of 45 bpm.

Such pacing control method is applied to common endocardial/epicardial pacing. However, for example, transcutaneous pacing (electrical stimulation) tends to cause pain, or even unbearable pain to the patient: however, in the existing pacing control method, pacing is initiated once the patient's heart rate decreases to the preset low-limit heart rate as described above, as a result, there is a problem of frequent pacing operations, which causes patients to be in pain from time to time due to pacing operations, resulting in a poor user experience and reducing the patient's use or compliance with medical apparatus/device.

BRIEF SUMMARY OF THE INVENTION

The technical problem to be solved by the present disclosure is to overcome the defect of frequent pacing in the pacing control method of the prior art, which tends to cause the patient to be in pain from time to time, resulting in a poor use experience. The purpose is to provide a pacing control method, a pacing control apparatus, and a medical device.

The present disclosure solves the above technical problem by the following technical solutions:

the present disclosure provides a pacing control method, comprising:

obtaining an actual heart rate of a patient;

determining whether the actual heart rate meets a preset low heart rate condition, and if so, performing cardiac pacing to the patient by using a preset pacing rate; wherein the preset low heart rate condition is used for representing that the patient is in a life-critical state.

It is no longer for the patient with bradycardia in the sense of traditional cardiac pacing therapy, but for the patient with severely too slow heart rate or even cardiac arrest due to basic or acute heart disease. The patient in the aforementioned life-critical state is taken as an object needing pacing support, where death is very likely to occur without pacing (the patient is in urgent need of help), that is, the pacing operation in the present disclosure is implemented only as a "necessary"/"life-saving" measure.

Specifically, by presetting trigger conditions for the pacing operation, pacing is performed on the patient by using a higher pacing rate only when the pacing is necessary, and the effect of timely and effective pacing is achieved to support the life of the patient: at the same time, the effect of avoiding, to a great extent, unnecessary pacing for the patient during daily use and the pain of the patient caused by pacing stimulation is also achieved, thereby improving the acceptability of the user and/or the use experience.

Preferably, the step of determining whether the actual heart rate meets the preset low heart rate condition, and if so, performing cardiac pacing to the patient by using the preset pacing rate comprises:

determining whether the actual heart rate is below a preset low heart rate, and if so, performing cardiac pacing to the patient by using the preset pacing rate.

By monitoring the real-time heart rate of the patient, it is determined that the patient is in urgent need of help when the real-time heart rate is below the given preset low heart rate (much below the preset low-limit heart rate in the existing pacing control method), that is, only when the heart rate of the patient is very low can cardiac pacing be triggered for the patient, and the effect of timely and effective pacing is achieved to support the life of the patient.

Preferably, the step of determining whether the actual heart rate meets the preset low heart rate condition, and if so, performing cardiac pacing to the patient by using the preset pacing rate comprises:

determining whether the actual heart rate is below the preset low heart rate, if so, obtaining a duration (that is, a first low heart rate duration) in which the actual heart rate of the patient is consecutively below the preset low heart rate, and when the first low heart rate duration reaches a preset duration, performing cardiac pacing to the patient by using the preset pacing rate.

By real-time monitoring of the patient's real-time heart rate, only when the actual heart rate is below the preset low heart rate and the first low heart rate duration of the actual heart rate reaches the preset low heart rate duration can pacing be triggered, which avoids unnecessary pacing operations when the patient's heart rate falls below the preset low heart rate by chance, and achieves better pacing monitoring function, which further improves the use experience of the user while ensuring patient safety.

Preferably, the preset pacing rate, the preset low heart rate and the preset low heart rate duration are parameters that can be reset by medical personnel according to the patient's condition.

Considering that different patients have different physical states and different degrees of acceptance of pacing, in order to enable each patient to receive targeted pacing therapy, the preset low heart rate, preset low heart rate duration and preset pacing rate that are suitable for each patient are finally determined by comprehensively considering multiple parameters such as medical history, current condition, medication use and pacing needs of each patient in advance, thereby optimizing patient experience while ensuring patient safety.

Preferably, the preset low heart rate is above 0 bpm and below or equal to 40 bpm: or, the preset low heart rate is above or equal to 10 bpm and below or equal to 30 bpm. The preset low heart rate is much below the preset low-limit heart rate in the existing pacing control method.

Preferably, the preset low heart rate duration ranges from 2 s to 5 min: or, the preset low heart rate duration ranges from 10 s to 60 s.

Preferably, the preset pacing rate comprises 40 bpm to 80 bpm.

Preferably, during execution of the step of performing cardiac pacing to the patient by using the preset pacing rate, the following steps are executed simultaneously:

obtaining the number of self heartbeats of the patient during a first pacing time period;

obtaining the total number of heartbeats of the patient during a given time period;

wherein the total number of heartbeats comprises the number of self heartbeats and number of pacing heartbeats; and the given time period comprises the first pacing time period, and a duration corresponding to the given time period is above or equal to a duration corresponding to the first pacing time period;

calculating a first ratio of the number of self heartbeats to the total number of heartbeats;

determining whether the first ratio is above or equal to a first given threshold, and if the first ratio is above or equal to the first given threshold, controlling to terminate pacing; if the first ratio is below the first given threshold, determining whether the first ratio is below or equal to a second given threshold, if the first ratio is below or equal to the second given threshold, continuing to execute the step of performing cardiac pacing to the patient by using the preset pacing rate; if the first ratio is above the second given threshold and below the first given threshold, reducing the preset pacing rate to a first pacing rate, and determining whether the first pacing rate is below a minimum pacing rate, if not, performing cardiac pacing to the patient by using the first pacing rate; and if so, performing cardiac pacing to the patient by using the minimum pacing rate; for example, reducing the preset pacing rate by 10 bpm, and performing cardiac pacing to the patient by using the reduced pacing rate; if the reduced pacing rate is below the minimum pacing rate, performing cardiac pacing to the patient by using the minimum pacing rate; wherein the minimum pacing rate ranges from 40 bpm to 60 bpm, commonly 50 bpm.

Herein, the ratio of the number of self heartbeats to the total number of heartbeats corresponding to the first given threshold is relatively high, and the ratio of the number of self heartbeats to the total number of heartbeats corresponding to the second given threshold is relatively low.

In order to perform pacing control in a timely and effective manner, after performing pacing to the patient by using the preset pacing rate for a period of time, the patient's heart rate is re-evaluated. If the self actual heart rate is above the preset pacing rate (which can be regarded as common heart rate) and lasts for a given duration, for example, 50 bpm or 60 bpm, it indicates that the pacing to the patient at the current pacing rate is effective, so that the patient recovers the self heart rate and is out of a life-critical situation. At this time, the pacing operation on the patient may be terminated. By terminating the pacing to the patient in time, the effect of minimizing the pain to the patient can be achieved.

If the self actual heart rates are still below or only a few heart rates are above a first preset pacing heart rate, that is, the common heart rate (50 bpm to 60 bpm, which can be adjusted by the doctor), it indicates that the patient's heart rate has not increased/recovered at the current pacing rate or the increase/recovery is not enough to support proper blood circulation. At this time, the patient's life safety is further ensured by continuing to perform pacing to the patient.

Preferably, the first given threshold ranges from 50% to 100%, the second given threshold ranges from 0 to 30%, and the minimum pacing rate ranges from 40 bpm to 60 bpm.

Preferably, the pacing control method also comprises:

obtaining the number of pacing heartbeats of the patient during the first pacing time period;

obtaining the total number of heartbeats of the patient during the given time period;

wherein the total number of heartbeats comprises the number of self heartbeats and the number of pacing heartbeats; and the given time period comprises the first pacing time period, and a duration corresponding to the given time period is above or equal to a duration corresponding to the first pacing time period;

calculating a second ratio of the number of pacing heartbeats to the total number of heartbeats;

determining whether the second ratio is below or equal to a third given threshold, and if the second ratio is below or equal to the third given threshold, controlling to terminate pacing; if the second ratio is above the third given threshold, determining whether the second ratio is above or equal to a fourth given threshold, if the second ratio is above or equal to the fourth given threshold, continuing to execute the step of performing cardiac pacing to the patient by using the preset pacing rate; if the second ratio is below the fourth given threshold and above the third given threshold, reducing the preset pacing rate to a first pacing rate, and determining whether the first pacing rate is below a minimum pacing rate, if not, performing cardiac pacing to the patient by using the first pacing rate; and if so, performing cardiac pacing to the patient by using the minimum pacing rate.

Preferably, the third given threshold ranges from 0 to 50%, the fourth given threshold ranges from 70 to 100%, and the minimum pacing rate ranges from 40 bpm to 60 bpm.

The present disclosure also provides a pacing control apparatus, comprising:

a heart rate acquisition module for obtaining an actual heart rate of a patient;

a first determination module for determining whether the actual heart rate meets a preset low heart rate condition, and if so, calling a pacing module to perform cardiac pacing to the patient by using a preset pacing rate; wherein the preset low heart rate condition is used for representing that the patient is in a life-critical state.

Preferably, the first determination module is used for determining whether the actual heart rate is below a preset low heart rate, and if so, calling the pacing module to perform cardiac pacing to the patient by using the preset pacing rate.

Preferably, the first determination module is used for determining whether the actual heart rate is below the preset low heart rate, and if so, calling a duration acquisition module to obtain a first low heart rate duration in which heart of the patient beats at the actual heart rate:

the first determination module is also used for calling the pacing module to perform cardiac pacing to the patient by using the preset pacing rate when the first low heart rate duration reaches a preset low heart rate duration.

Preferably, the preset pacing rate, the preset low heart rate and the preset low heart rate duration are parameters that can be reset according to the patient's condition.

Preferably, the preset low heart rate is above 0 bpm and below or equal to 40 bpm: or, the preset low heart rate is above or equal to 10 bpm and below or equal to 30 bpm.

Preferably, the preset low heart rate duration ranges from 2 s to 5 min: or, the preset low heart rate duration ranges from 10 s to 60 s.

Preferably, the preset pacing rate comprises 40 bpm to 80 bpm.

Preferably, the pacing control apparatus also comprises:

a self-heartbeat number acquisition module for obtaining the number of self heartbeats of the patient during a first pacing time period;

a total-heartbeat number acquisition module for obtaining the total number of heartbeats of the patient during a given time period;

wherein the given time period comprises the first pacing time period, and a duration corresponding to the given time period is above or equal to a duration corresponding to the first pacing time period;

a first ratio calculation module for calculating a first ratio of the number of self heartbeats to the total number of heartbeats;

a second determination module for determining whether the first ratio is above or equal to a first given threshold, and if the first ratio is above or equal to the first given threshold, controlling to terminate pacing; if the first ratio is below the first given threshold, determining whether the first ratio is below or equal to a second given threshold, if the first ratio is below or equal to the second given threshold, calling a pacing module to perform cardiac pacing to the patient by using the preset pacing rate; if the first ratio is above the second given threshold and below the first given threshold, calling the pacing module to reduce the preset pacing rate to a first pacing rate, and determining whether the first pacing rate is below a minimum pacing rate, if not, performing cardiac pacing to the patient by using the first pacing rate; and if so, performing cardiac pacing to the patient by using the minimum pacing rate; for example, reducing the preset pacing rate by 10 bpm, and performing cardiac pacing to the patient by using the reduced pacing rate; if the reduced pacing rate is below the minimum pacing rate, performing cardiac pacing to the patient by using the minimum pacing rate; wherein the minimum pacing rate ranges from 40 bpm to 60 bpm, commonly 50 bpm.

Herein, the ratio of the number of self heartbeats to the total number of heartbeats corresponding to the first given threshold is relatively high, and the ratio of the number of self heartbeats to the total number of heartbeats corresponding to the second given threshold is relatively low.

Preferably, the first given threshold ranges from 50 to 100%, the second given threshold ranges from 0 to 30%, and the minimum pacing rate ranges from 40 bpm to 60 bpm.

Preferably, the pacing control apparatus also comprises:

a pacing-heartbeat number acquisition module for obtaining the number of pacing heartbeats of the patient during the first pacing time period;

a total-heartbeat number acquisition module for obtaining the total number of heartbeats of the patient during the given time period;

wherein the total number of heartbeats comprises the number of self heartbeats and the number of pacing heartbeats; and the given time period comprises the first pacing time period, and a duration corresponding to the given time period is above or equal to a duration corresponding to the first pacing time period;

a second ratio calculation module for calculating a second ratio of the number of pacing heartbeats to the total number of heartbeats;

a third determination module for determining whether the second ratio is below or equal to a third given threshold, if the second ratio is below or equal to the third given threshold, controlling to terminate pacing; if the second ratio is above the third given threshold, determining whether the second ratio is above or equal to a fourth given threshold, if the second ratio is above or equal to the fourth given threshold, calling the pacing module to continue to perform cardiac pacing to the patient by using a preset pacing rate; if the second ratio is below the fourth given threshold and above the third given threshold, calling the pacing module to reduce the preset pacing rate to a first pacing rate, and determining whether the first pacing rate is below the minimum pacing rate, if not, performing cardia pacing to the patient by using the first pacing rate; and if so, performing cardiac pacing to the patient by using the minimum pacing rate.

Preferably, the third given threshold ranges from 0 to 50%, the fourth given threshold ranges from 70 to 100%, and the minimum pacing rate ranges from 40 bpm to 60 bpm.

The present disclosure also provides a medical device, comprising the pacing control apparatus as described above.

Preferably, the medical device comprises a wearable cardioverter defibrillator (WCD), an external defibrillator (for example, AED), a subcutaneous implantable cardioverter defibrillator (SICD), or a mechanical circulatory support device (MCS).

On the basis of common knowledge in the art, each of the preferred conditions can be combined in any way to obtain each preferred embodiment of the present disclosure.

The positive progressive effect of the present disclosure is that:

the present disclosure is no longer for the patient with bradycardia in the traditional sense, but takes the patient in the life-critical state where the heart rate is severely too slow or even cardiac arrest occurs due to basic or acute heart disease as an object needing pacing support: by presetting the trigger conditions for the pacing operation, pacing is performed on the patient by using a higher pacing rate only when the pacing is necessary, and the effect of timely and effective pacing is achieved to support the life of the patient, and pacing is terminated when the self heart rate of the patient recovers to a certain level: at the same time, the effect of avoiding, to a great extent, unnecessary pacing for the patient during daily use and the pain of the patient caused by pacing stimulation is also achieved, thereby improving the user's acceptability, compliance and use experience of medical apparatus.

BRIEF DESCRIPTION OF THE DRAWINGS

FIG. 1 is a first flow chart of a pacing control method according to Embodiment 1 of the present disclosure.

FIG. 2 is a second flow chart of the pacing control method according to Embodiment 1 of the present disclosure.

Figure 3:
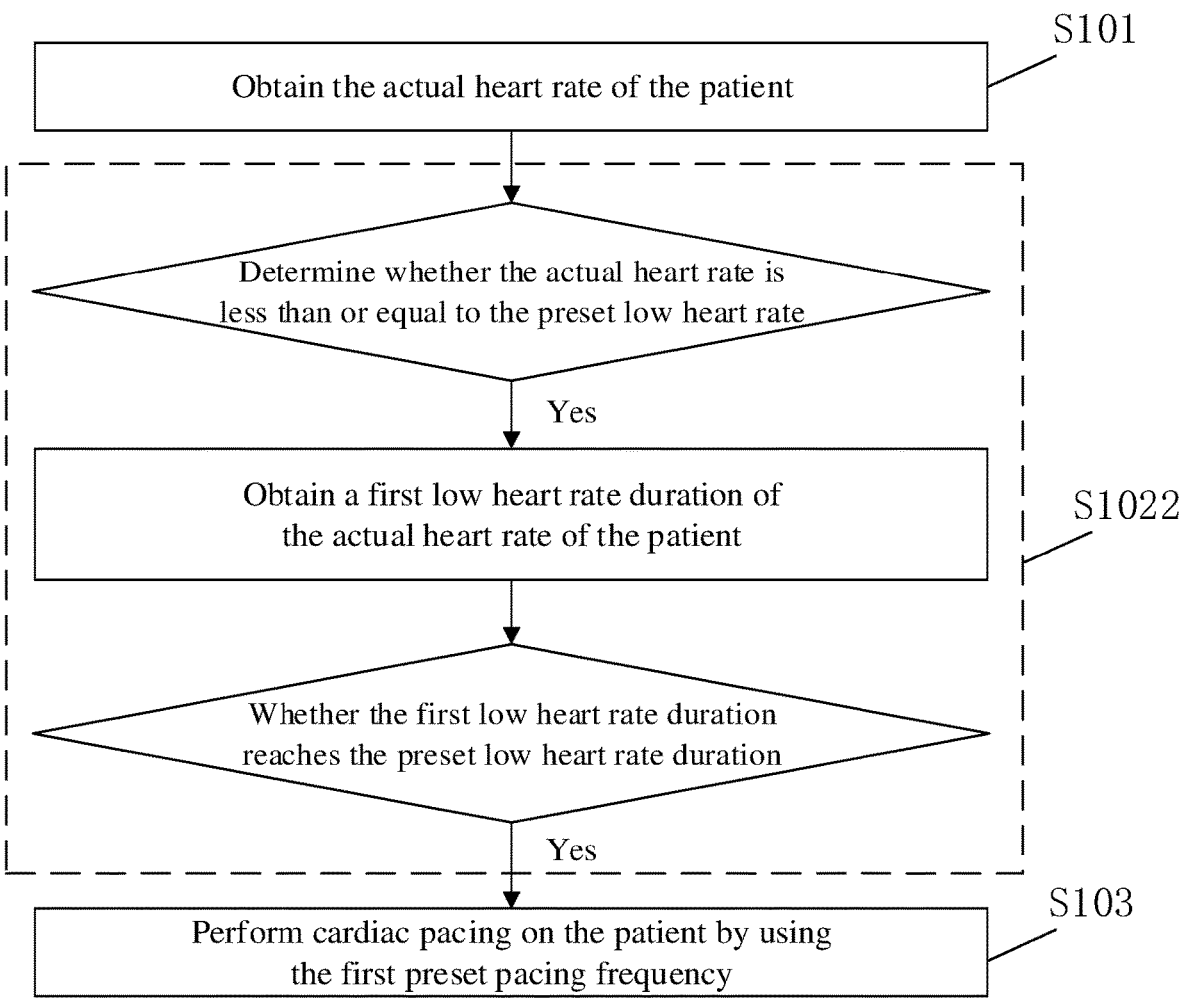

FIG. 3 is a third flow chart of the pacing control method according to Embodiment 1 of the present disclosure.

Figure 4:
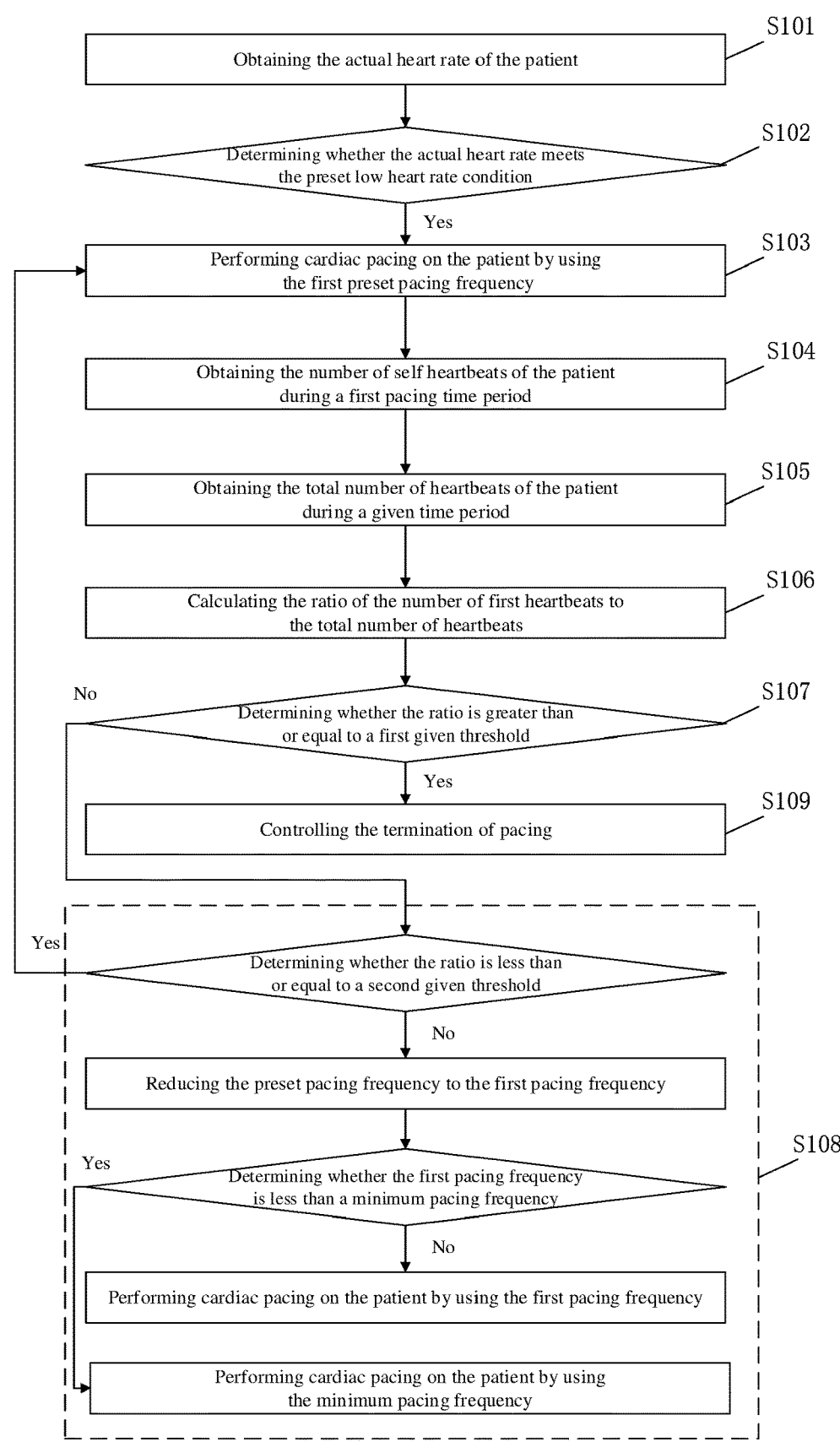

FIG. 4 is a first flow chart of a pacing control method according to Embodiment 2 of the present disclosure.

Figure 5:
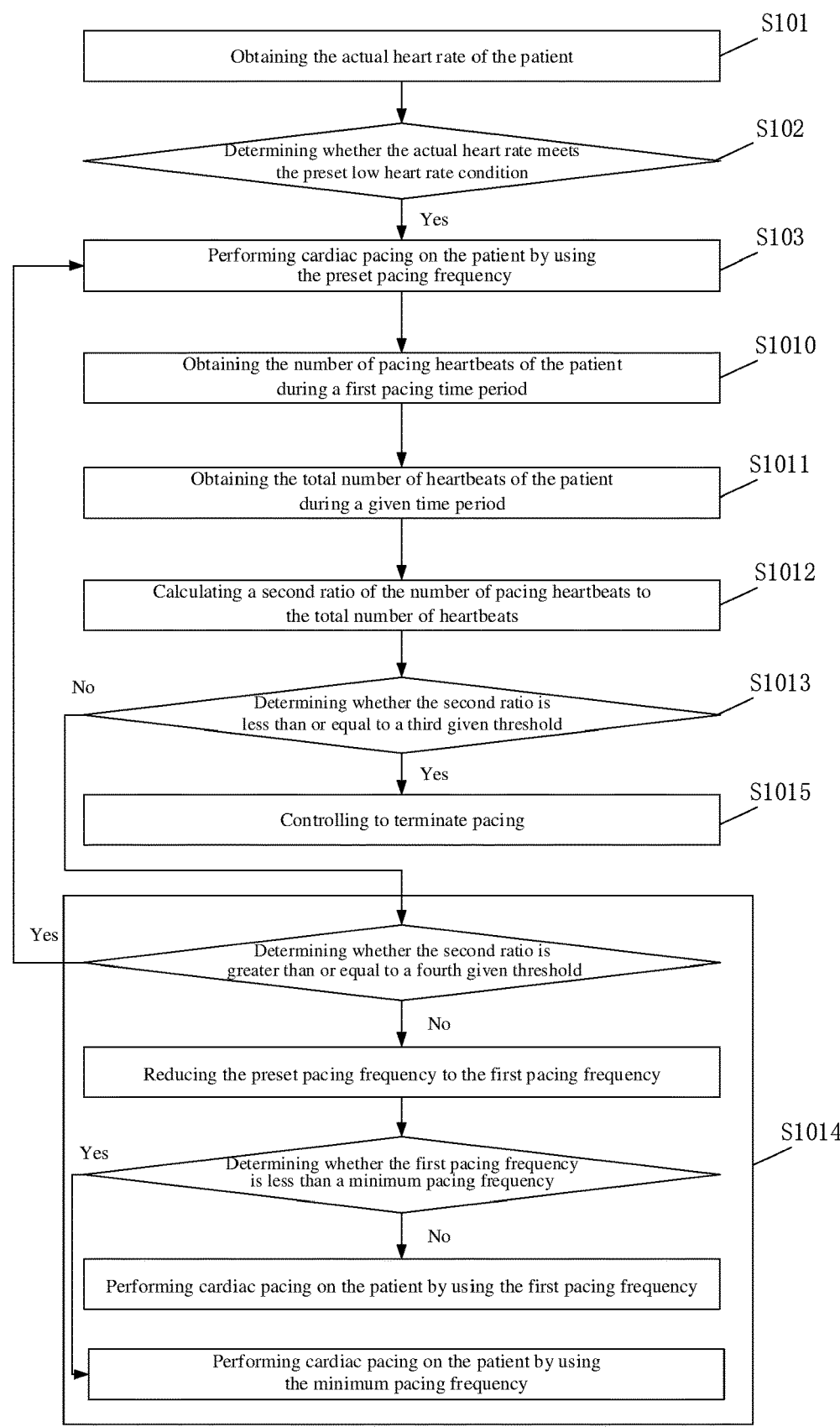

FIG. 5 is a second flow chart of the pacing control method according to Embodiment 2 of the present disclosure.

Figure 6:
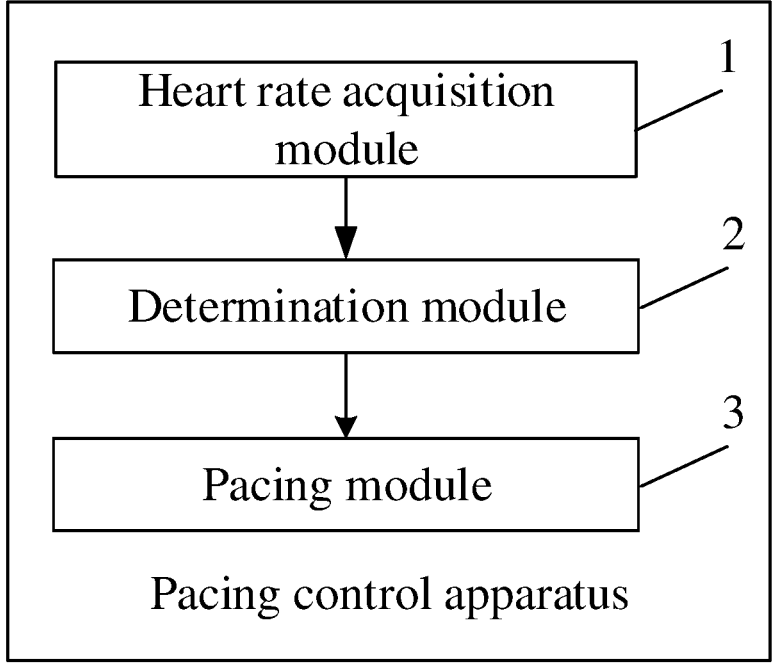

FIG. 6 is a first schematic structural diagram of a pacing control apparatus according to Embodiment 3 of the present disclosure.

Figure 7:
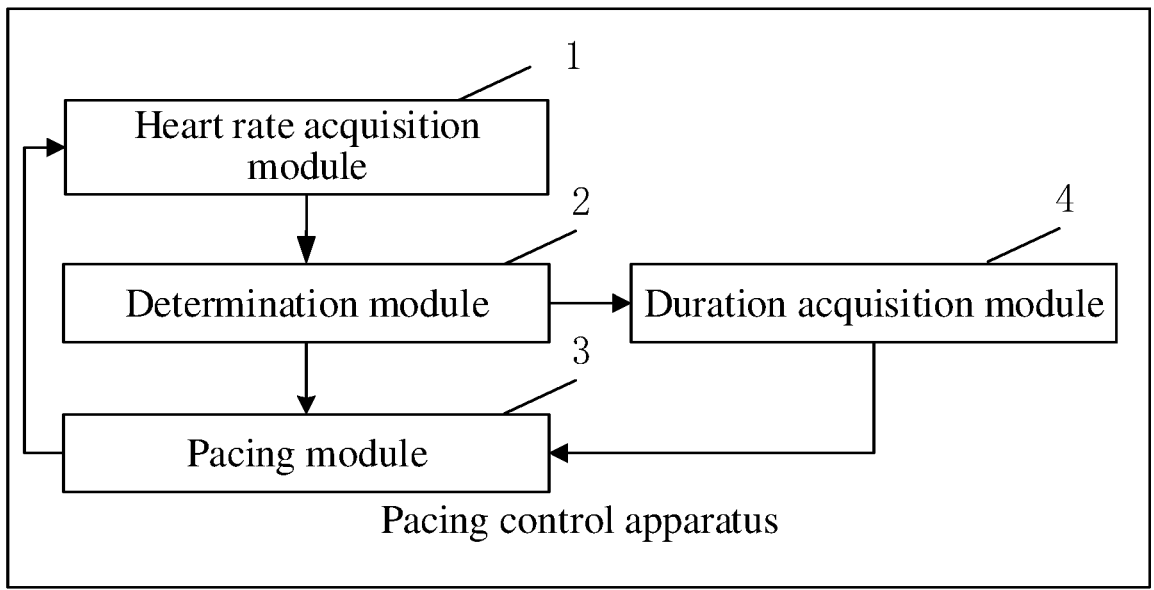

FIG. 7 is a second schematic structural diagram of the pacing control apparatus according to Embodiment 3 of the present disclosure.

Figure 8:
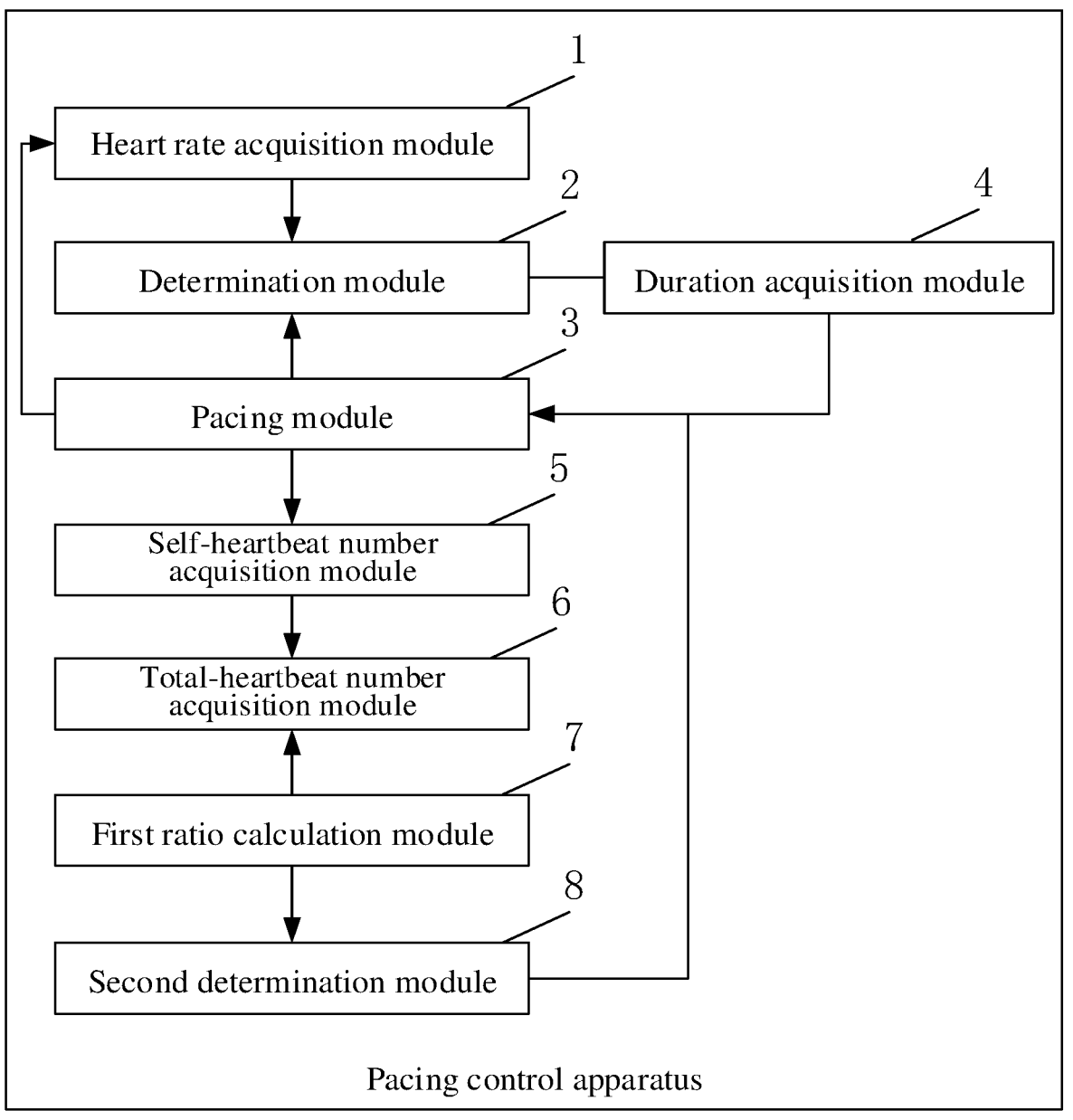

FIG. 8 is a first schematic structural diagram of a pacing control apparatus according to Embodiment 4 of the present disclosure.

Figure 9:
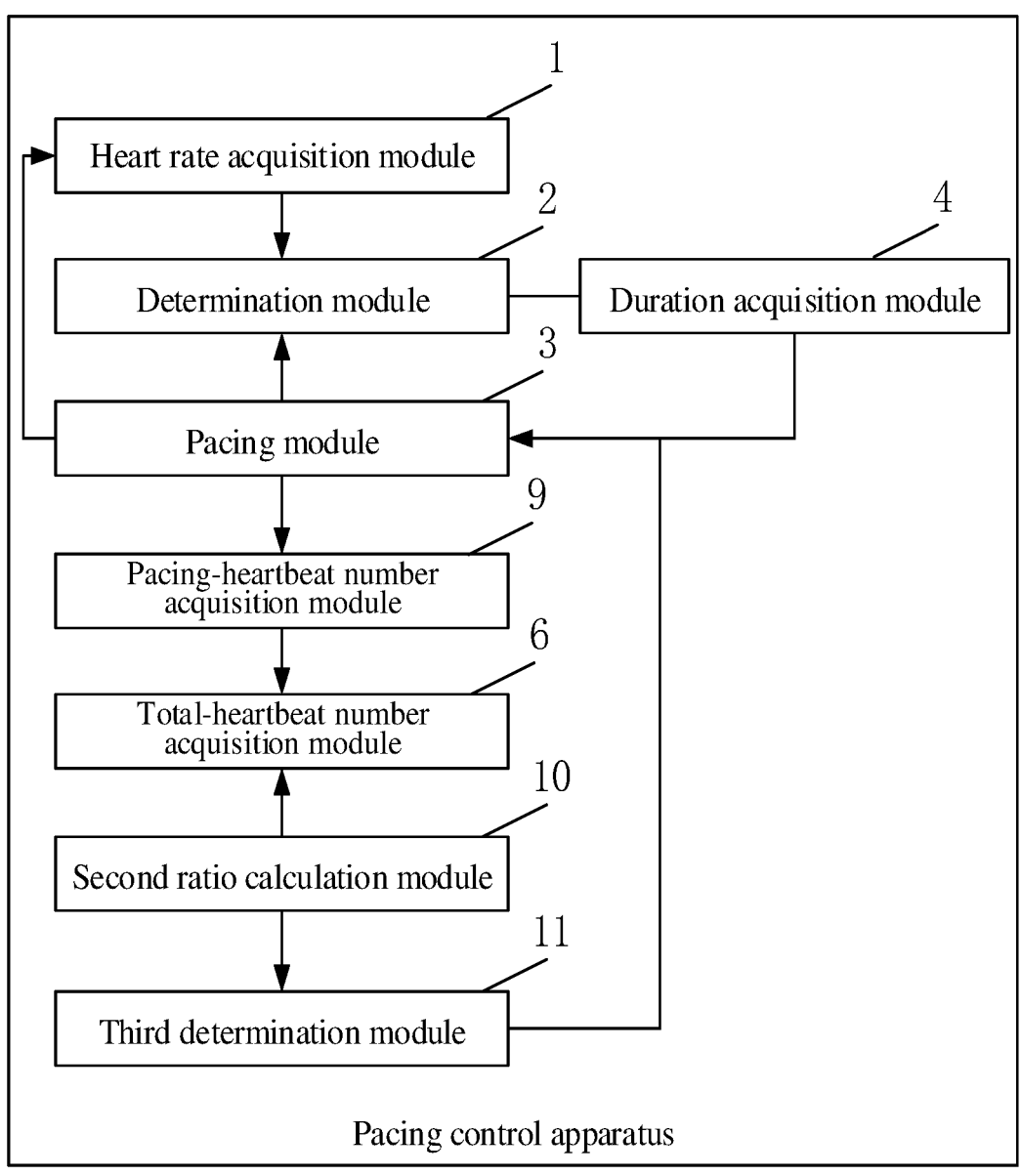

FIG. 9 is a second schematic structural diagram of the pacing control apparatus according to Embodiment 4 of the present disclosure.

DETAILED DESCRIPTION OF THE INVENTION

The present disclosure is further illustrated below by means of embodiments, but the present disclosure is not thereby limited to the scope of the embodiments.

Embodiment 1

As shown in FIG. 1, a pacing control method of the present embodiment comprises:

S101, obtaining an actual heart rate of a patient;

S102, determining whether the actual heart rate meets a preset low heart rate condition, and if so, performing S103;

S103, performing cardiac pacing to the patient by using a preset pacing rate; wherein the preset low heart rate condition is used for representing that the patient is in a life-critical state.

It is no longer for the patient with bradycardia in the traditional sense, but for the patient with severely too slow heart rate or even cardiac arrest due to basic or acute heart disease. The patient who is in the aforementioned life-critical state is taken as an object needing pacing support, where death is very likely to occur without pacing (the patient is in urgent need of help), that is, the pacing operation in the present disclosure is implemented only as a "necessary"/"life-saving" measure.

Specifically, by presetting the trigger conditions for the pacing operation, pacing is performed on the patient by using a higher pacing rate only when the pacing is necessary, and the effect of timely and effective pacing is achieved to support the life of the patient: at the same time, the effect of avoiding, to a great extent, unnecessary pacing for the patient during daily use and the pain of the patient caused by pacing stimulation is also achieved, thereby improving the user's acceptability, compliance and use experience of medical apparatus.

Specifically, as shown in FIG. 2, step S102 comprises:

S1021, determining whether the actual heart rate is below a preset low heart rate, and if so, performing S103.

By monitoring the real-time heart rate of the patient, it is determined that the patient is in urgent need of help when the real-time heart rate is below the given preset low heart rate (much below the preset low-limit heart rate in the existing pacing control method), that is, only when the heart rate of the patient is very low can cardiac pacing be triggered for the patient, and the effect of timely and effective pacing is achieved to support the life of the patient. Alternatively, as shown in FIG. 3, step S102 comprises:

S1022, determining whether the actual heart rate is below the preset low heart rate, if so, obtaining a first low heart rate duration in which heart of the patient beats at the actual heart rate: and determining whether the first low heart rate duration reaches a preset low heart rate duration, if so, performing S103.

By real-time monitoring of the patient's real-time heart rate, only when the actual heart rate is below the preset low heart rate and the first low heart rate duration of the actual heart rate reaches the preset low heart rate duration can pacing be triggered. For example, when the preset low-limit heart rate is set to 45 bpm, if the monitored patient's heart rate (one heartbeat or R-R interval) is below 45 bpm for the first time, pacing will not be performed on the patient immediately, but the next or even subsequent multiple heartbeats or R-R intervals will be continuously monitored, and when the monitored patient's heart rate is consecutively below 45 bpm will pacing be triggered. It avoids unnecessary pacing operations when the patient's heart rate falls below the preset low heart rate by chance, and achieves better pacing monitoring function, which further improves the use experience of the user while ensuring patient safety.

In an embodiment, the preset low heart rate is above 0 bpm and below or equal to 40 bpm, preferably, the preset low heart rate includes 10 bpm to 30 bpm, and further, the preset low heart rate may be set to 20 bpm. It should be noted that the pacing control method of the present embodiment is still applicable when cardiac arrest occurs, that is, when the real-time heart rate of the patient is 0 bpm, achieving timely pacing to save the patient's life in an extreme state where the patient has no heartbeat.

The preset low heart rate duration includes 2 s to 5 min (that is, 2 seconds to 5 minutes). The preset low heart rate duration may be adjusted and determined according to the physical states of different patients or other actual conditions. The preset low heart rate duration is within the scope of protection of the present disclosure as long as it can be reasonably applied in the technical solutions of the present disclosure during the actual pacing process.

In addition, the preset low heart rate duration may also include 2 s to 60 s, preferably, the preset low heart rate duration is 2 s to 20 s, and further, the preset low heart rate duration may be set to 10 s, and the preset low heart rate duration may also include 10 s to 60 s.

The preset pacing rate includes 35 bpm to 90 bpm. The preset pacing rate can be adjusted and determined according to the physical states of different patients or other actual conditions. The preset pacing rate is within the scope of protection of the present disclosure as long as it can be reasonably applied in the technical solutions of the present disclosure during the actual pacing process.

In addition, the preset pacing rate may also include 40 bpm to 80 bpm, preferably, the preset pacing rate is 50 bpm to 65 bpm. Further, the preset pacing rate may be set to 60 bpm.

The preset pacing rate, the preset low heart rate and the preset low heart rate duration in the present embodiment are parameters that can be reset according to the specific conditions of different patients. Considering that there are certain differences in the physical states of different patients, in order to enable each patient to receive targeted pacing therapy, the preset low heart rate, preset low heart rate duration and preset pacing rate that are suitable for each patient are finally determined by comprehensively considering multiple parameters such as medical history, current condition, medication use and pacing needs of each patient in advance, thereby optimizing patient experience while ensuring patient safety.

It should be noted that all parameter values of the present embodiment can be reset according to actual conditions.

In the present embodiment, for the patient in the life-critical state where the heart rate is severely too slow or even cardiac arrest occurs, by presetting the trigger conditions for the pacing operation, pacing is performed on the patient by using a higher pacing rate only when the pacing is necessary, and the effect of timely and effective pacing is achieved to support the life of the patient, and pacing is terminated when the self heart rate of the patient recovers to a certain level; at the same time, the effect of avoiding, to a great extent, unnecessary pacing for the patient during daily use and the pain of the patient caused by pacing stimulation is also achieved, and especially pacing to occasional bradycardia, non-severe bradycardia, or transient arrest cannot be triggered, thereby improving the user's acceptability, compliance and use experience of medical apparatus.

Embodiment 2

A pacing control method of the present embodiment is a further improvement on Embodiment 1, specifically:

as shown in FIG. 4, after step S103, the method also comprises:

S104, obtaining the number of self heartbeats of the patient during a first pacing time period;

wherein the number of heartbeats obtained at this time is the number of heartbeats on patient's self, that is, the number of non-pacing heartbeats.

S105, obtaining the total number of heartbeats of the patient during a given time period:

wherein the given time period includes the first pacing time period, and the duration corresponding to the given time period is above or equal to the duration corresponding to the first pacing time period: it is certain that in addition to using time for limitation, the total number of heartbeats may also be used instead of time for limitation (that is, the total number of heartbeats is above or equal to the number of self heartbeats).

Both the duration corresponding to the first pacing time period and the duration corresponding to the given time period can be set and adjusted according to actual needs.

The process of obtaining the number of self heartbeats, the number of pacing heartbeats and the total number of heartbeats is well established in the art and therefore will not be repeated here.

S106, calculating a first ratio of the number of self heartbeats to the total number of heartbeats:

S107, determining whether the first ratio is above or equal to a first given threshold, if so, performing step S109: if not, performing step S108;

S108, determining whether the first ratio is below or equal to a second given threshold, if so, continuing to execute step S103: if not, reducing the preset pacing rate to a first pacing rate, and determining whether the first pacing rate is below a minimum pacing rate, for example, reducing the preset pacing rate by 10 bpm, and performing cardiac pacing to the patient by using the reduced pacing rate; if not, performing cardiac pacing to the patient by using the first pacing rate; if so, performing cardiac pacing to the patient by using the minimum pacing rate. Herein, the minimum pacing rate ranges from 40 bpm to 60 bpm, commonly 50 bpm.

Herein, the minimum pacing rate is a preset pacing threshold, and it is certain that it can be re-determined and adjusted according to actual needs.

The ratio of the number of self heartbeats to the total number of heartbeats corresponding to the first given threshold is relatively high, and the ratio of the number of self heartbeats to the total number of heartbeats corresponding to the second given threshold is relatively low.

Specifically, the first given threshold ranges from 50% to 100%, the second given threshold ranges from 0 to 30%, and the minimum pacing rate ranges from 40 bpm to 60 bpm.

Herein, steps S104 to S108 are continuously executed during the pacing process until pacing is terminated, so as to perform pacing control as timely and effectively as possible.

S109, controlling to terminate pacing, during which pacing can be manually terminated or adjusted in real time.

Specifically, the pacing operation may be programmed to last for a given duration, for example, one minute (from several seconds to several minutes, specifically, it can be set and adjusted according to actual needs: in addition, the pacing operation may be manually terminated by a programmable controller, an operation button or other means according to actual needs), and the number of self heartbeats of the patient and the total number of heartbeats during this time period are accumulated, then the ratio of the number of self heartbeats to the total number of heartbeats of the patient during the pacing phase is calculated; if the ratio is above a certain given value (50 to 100%, preferably for example 90%, programmable), it indicates that the pacing is effective and the self heart rate has recovered to a level higher than the preset pacing rate, so it is determined that the pacing can be terminated; if the ratio is below a certain given value (0 to 30%, preferably for example 10%, programmable), it indicates that the patient's autonomic heart rate has not recovered and pacing support is still needed, so pacing is continued using the preset pacing rate. Otherwise, the pacing rate is reduced by 10 bpm for pacing, and the above process continues until the pacing rate reaches the default minimum pacing rate (in the range of 40 bpm to 60 bpm, preferably for example 50 bpm).

In another embodiment, as shown in FIG. 5, after step S103, the method also comprises:

S1010, obtaining the number of pacing heartbeats of the patient during the first pacing time period;

S1011, obtaining the total number of heartbeats of the patient during the given time period;

wherein the total number of heartbeats includes the number of self heartbeats and the number of pacing heartbeats;

the given time period includes the first pacing time period, and the duration corresponding to the given time period is above or equal to the duration corresponding to the first pacing time period;

S1012, calculating a second ratio of the number of pacing heartbeats to the total number of heartbeats;

S1013, determining whether the second ratio is below or equal to a third given threshold, if the second ratio is below or equal to the third given threshold, controlling to execute step S1015; if the second ratio is above the third given threshold, executing step S1014;

S1014, determining whether the second ratio is above or equal to a fourth given threshold, if the second ratio is above or equal to the fourth given threshold, continuing to execute step S103: if the second ratio is below the fourth given threshold and above the third given threshold, reducing the preset pacing rate to the first pacing rate, and determining whether the first pacing rate is below the minimum pacing rate, if not, performing cardiac pacing to the patient by using the first pacing rate; and if so, performing cardiac pacing to the patient by using the minimum pacing rate.

Herein, the third given threshold ranges from 0 to 50%, the fourth given threshold ranges from 70 to 100%, and the minimum pacing rate ranges from 40 bpm to 60 bpm.

Herein, steps S1010 to S1014 are continuously executed during the pacing process until pacing is terminated, so as to perform pacing control as timely and effectively as possible.

S1015, controlling to terminate pacing, during which pacing may be manually terminated or adjusted in real time.

In order to perform pacing control in a timely and effective manner, the self heart rate of the patient is collected when performing pacing to the patient by using the preset pacing rate, and after a period of time, the self heart rate of the patient is re-evaluated. If the self actual heart rate is above the preset pacing rate (which may be regarded as common heart rate) and lasts for a given duration, for example, 50 bpm or 60 bpm, it indicates that the pacing to the patient at the current pacing rate is effective, so that the patient recovers the self heart rate and is out of a life-critical situation. At this time, the pacing operation on the patient may be terminated. By terminating the pacing to the patient in time, the effect of minimizing the pain to the patient can be achieved.

If the self actual heart rates are below or only a few heart rates are above the first preset pacing heart rate, that is, the common heart rate (50 bpm to 60 bpm, which can be adjusted by the doctor), it indicates that the patient's heart rate has not increased/recovered at the current pacing rate or the increase/recovery is not enough to support proper blood circulation. At this time, the patient's life safety is further ensured by continuing to perform pacing to the patient.

It is certain that the above values can be preset or adjusted according to the doctor's clinical judgment, so as to adapt to different patients and meet the needs of different patients, further improving the use experience of the user.

It should be noted that all parameter values of the present embodiment may be reset according to actual conditions.

In the present embodiment, for the patient in the life-critical state where the heart rate is severely too slow or even cardiac arrest occurs, by presetting the trigger conditions for the pacing operation, pacing is performed on the patient by using a higher pacing rate only when the pacing is necessary, and the effect of timely and effective pacing is achieved to support the life of the patient, and pacing is terminated when the self heart rate of the patient recovers to a certain level; at the same time, the effect of avoiding, to a great extent, unnecessary pacing for the patient during daily use and the pain of the patient caused by pacing stimulation is also achieved, and especially pacing to occasional bradycardia, non-severe bradycardia, or transient arrest cannot be triggered, thereby improving the user's acceptability, compliance and use experience of medical apparatus. In addition, after the pacing operation is implemented, the effectiveness of the pacing operation on the patient is monitored in a timely manner, and the pacing rate is adaptively adjusted to ensure timely and effective ventricular capture, guaranteeing the patient's life safety.

Embodiment 3

As shown in FIG. 6, a pacing control apparatus of the present embodiment comprises a heart rate acquisition module 1, a determination module 2 and a pacing module 3.

The heart rate acquisition module 1 is used for obtaining an actual heart rate of a patient:

the determination module 2 is used for determining whether the actual heart rate meets a preset low heart rate condition, and if so, calling the pacing module 3 to perform cardiac pacing to the patient by using a preset pacing rate; wherein the preset low heart rate condition is used for representing that the patient is in a life-critical state.

It is no longer for the patient with bradycardia in the traditional sense, but for the patient with severely too slow heart rate or even cardiac arrest. The patient who is in the aforementioned life-critical state is taken as an object needing pacing support, where death is very likely to occur without pacing (the patient is in urgent need of help), that is, the pacing operation in the present disclosure is implemented only as a "necessary"/"life-saving" measure.

Specifically, by presetting the trigger conditions for the pacing operation, pacing is performed on the patient by using a higher pacing rate only when the pacing is necessary, and the effect of timely and effective pacing is achieved to support the life of the patient: at the same time, the effect of avoiding, to a great extent, unnecessary pacing for the patient during daily use and the pain of the patient caused by pacing stimulation is also achieved, and especially pacing to occasional bradycardia, non-severe bradycardia, or transient arrest cannot be triggered, thereby improving the user's acceptability, compliance and use experience of medical apparatus.

Specifically, the determination module 2 is used for determining whether the actual heart rate is below a preset low heart rate, and if so, calling the pacing module 3 to perform cardiac pacing to the patient by using the preset pacing rate.

By monitoring the real-time heart rate of the patient, it is determined that the patient is in urgent need of help when the real-time heart rate is below the given preset low heart rate (much below the preset low-limit heart rate in the existing pacing control method), that is, only when the heart rate of the patient is very low can cardiac pacing be triggered for the patient, and the effect of timely and effective pacing is achieved to support the life of the patient. Alternatively, as shown in FIG. 7, the pacing control apparatus of the present embodiment also comprises a duration acquisition module 4.

The determination module 2 is used for determining whether the actual heart rate is below the preset low heart rate, and if so, calling the duration acquisition module 4 to obtain a first low heart rate duration in which heart of the patient beats at the actual heart rate:

the determination module 2 is also used for calling the pacing module 3 to perform cardiac pacing to the patient by using the preset pacing rate when the first low heart rate duration reaches a preset low heart rate duration.

By real-time monitoring of the patient's real-time heart rate, only when the actual heart rate is below the preset low heart rate and the first low heart rate duration of the actual heart rate reaches or exceeds the preset low heart rate duration can pacing be triggered, which avoids unnecessary pacing operations when the patient's heart rate falls below the preset low heart rate by chance, and achieves better pacing monitoring function, which further improves the use experience of the user while ensuring patient safety.

In an embodiment, the preset low heart rate is above 0 bpm and below or equal to 40 bpm, the preset low heart rate is much below the preset low-limit heart rate in the existing pacing control method, and the preset low heart rate can be set to ensure ventricular capture of the patient after the pacing process. Preferably, the preset low heart rate includes 10 bpm to 30 bpm, and further, the preset low heart rate may be set to 20 bpm.

The preset low heart rate duration includes 2 s to 5 min (that is, 2 seconds to 5 minutes). The preset low heart rate duration can be adjusted and determined according to the physical states of different patients or other actual conditions. The preset low heart rate duration is within the scope of protection of the present disclosure as long as it can be reasonably applied in the technical solutions of the present disclosure during the actual pacing process. It should be noted that the pacing control method of the present embodiment is still applicable when cardiac arrest occurs, that is, when the real-time heart rate of the patient is 0 bpm, achieving timely pacing to save the patient's life in an extreme state where the patient has no heartbeat.

The preset low heart rate duration may include 2 s to 60 s, preferably, the preset low heart rate duration is 2 s to 20 s, and further, the preset low heart rate duration may be set to 10 s, and the preset low heart rate duration may also include 10 s to 60 s.

The preset pacing rate includes 35 bpm to 90 bpm. The preset pacing rate may be adjusted and determined according to the physical states of different patients or other actual conditions. The preset pacing rate is within the scope of protection of the present disclosure as long as it can be reasonably applied in the technical solutions of the present disclosure during the actual pacing process.

In addition, the preset pacing rate may also include 40 bpm to 80 bpm, preferably, the preset pacing rate is 50 bpm to 65 bpm. Further, the preset pacing rate may be set to 60 bpm.

The preset pacing rate, the preset low heart rate and the preset low heart rate duration of the present embodiment are parameters that can be reset according to the specific conditions of different patients. Considering that there are certain differences in the physical states of different patients, in order to enable each patient to receive targeted pacing therapy, the preset low heart rate, preset low heart rate duration and preset pacing rate that are suitable for each patient are finally determined by comprehensively considering multiple parameters such as medical history, current condition, medication use and pacing needs of each patient in advance, thereby optimizing patient experience while ensuring patient safety.

It should be noted that all parameter values of the present embodiment can be reset according to actual conditions.

In the present embodiment, for the patient in the life-critical state where the heart rate is severely too slow or even cardiac arrest occurs, by presetting the trigger conditions for the pacing operation, pacing is performed on the patient by using a higher pacing rate only when the pacing is necessary, and the effect of timely and effective pacing is achieved to support the life of the patient, and pacing is terminated when the self heart rate of the patient recovers to a certain level; at the same time, the effect of avoiding, to a great extent, unnecessary pacing for the patient during daily use and the pain of the patient caused by pacing stimulation is also achieved, and especially pacing to occasional bradycardia, non-severe bradycardia, or transient arrest cannot be triggered, thereby improving the user's acceptability, compliance and use experience of medical apparatus.

Embodiment 4

A pacing control apparatus of the present embodiment is a further improvement on Embodiment 3, specifically:

as shown in FIG. 8, the pacing control apparatus of the present embodiment comprises a self-heartbeat number acquisition module 5, a total-heartbeat number acquisition module 6, a first ratio calculation module 7 and a second determination module 8.

The self-heartbeat number acquisition module 5 is used for obtaining the number of self heartbeats of the patient during a first pacing time period:

the total-heartbeat number acquisition module 6 is used for obtaining the total number of heartbeats of the patient during a given time period;

wherein the total number of heartbeats includes the number of self heartbeats and the number of pacing heartbeats;

the given time period includes the first pacing time period, and the duration corresponding to the given time period is above or equal to the duration corresponding to the first pacing time period;

the first ratio calculation module 7 is used for calculating a first ratio of the number of self heartbeats to the total number of heartbeats;

the second determination module 8 is used for determining whether the first ratio is above or equal to a first given threshold, if the first ratio is above or equal to a first given threshold, calling the pacing module 3 to control to terminate pacing; if the first ratio is below the first given threshold, determining whether the first ratio is below or equal to a second given threshold, if the first ratio is below or equal to the second given threshold, calling the pacing module 3 to continue to perform cardiac pacing to the patient; if the first ratio is above or equal to the second given threshold and below or equal to the first given threshold, calling the pacing module 3 to reduce the preset pacing rate to a first pacing rate, and determining whether the first pacing rate is below a minimum pacing rate for example, reducing the preset pacing rate by 10 bpm, and performing cardiac pacing to the patient by using the reduced pacing rate; if not, performing cardiac pacing to the patient by using the first pacing rate; if so, performing cardiac pacing to the patient by using the minimum pacing rate. Herein, the minimum pacing rate ranges from 40 bpm to 60 bpm, commonly 50 bpm.

Herein, the minimum pacing rate is a preset pacing threshold, and it is certain that it may be re-determined and adjusted according to actual needs.

The ratio of the number of self heartbeats to the total number of heartbeats corresponding to the first given threshold is relatively high, and the ratio of the number of self heartbeats to the total number of heartbeats corresponding to the second given threshold is relatively low.

Specifically, the first given threshold ranges from 50 to 100%, the second given threshold ranges from 0 to 30%, and the minimum pacing rate ranges from 40 bpm to 60 bpm.

The pacing operation may be programmed to last for a given duration, for example, one minute (from several seconds to several minutes, specifically, the given duration can be set and adjusted according to actual needs: in addition, the pacing operation may be manually terminated by a programmable controller, an operation button or other means according to actual needs), and the number of self heartbeats of the patient and the total number of heartbeats during the time period are accumulated, then the ratio of the number of self heartbeats to the total number of heartbeats of the patient during the pacing phase is calculated; if the ratio is above a certain given value (50 to 100%, preferably for example 90%, programmable), it indicates that the pacing is effective and the self heart rate has recovered to a level higher than the preset pacing rate, so it is determined that the pacing may be terminated; if the ratio is below a given value (0 to 30%, preferably for example 10%, programmable), it indicates that the patient's autonomic heart rate has not recovered and pacing support is still needed, so pacing is continued using the preset pacing rate. Otherwise, the pacing rate is reduced by 10 bpm for pacing, and the above process continues until the pacing rate reaches the default minimum pacing rate (in the range of 40 bpm to 60 bpm, preferably for example 50 bpm).

As shown in FIG. 9, the pacing control apparatus of the present embodiment also comprises:

a pacing-heartbeat number acquisition module 9 for obtaining the number of pacing heartbeats of the patient during the first pacing time period;

the total-heartbeat number acquisition module 6 for obtaining the total number of heartbeats of the patient during the given time period;

wherein the total number of heartbeats includes the number of self heartbeats and the number of pacing heartbeats;

the given time period includes the first pacing time period, and the duration corresponding to the given time period is above or equal to the duration corresponding to the first pacing time period;

a second ratio calculation module 10 for calculating a second ratio of the number of pacing heartbeats to the total number of heartbeats;

a third determination module 11 for determining whether the second ratio is below or equal to a third given threshold, if the second ratio is below or equal to the third given threshold, controlling to terminate pacing; if the second ratio is above the third given threshold, determining whether the second ratio is above or equal to a fourth given threshold, if the second ratio is above or equal to the fourth given threshold, calling the pacing module 3 to continue to perform cardiac pacing to the patient by using the preset pacing rate; if the second ratio is below the fourth given threshold and above the third given threshold, calling the pacing module 3 to reduce the preset pacing rate to the first pacing rate, and determining whether the first pacing rate is below the minimum pacing rate, if not, performing cardiac pacing to the patient by using the first pacing rate; and if so, performing cardiac pacing to the patient by using the minimum pacing rate.

Herein, the third given threshold ranges from 0 to 50%, the fourth given threshold ranges from 70 to 100%, and the minimum pacing rate ranges from 40 bpm to 60 bpm.

In order to perform pacing control in a timely and effective manner, the self heart rate of the patient is collected when performing pacing to the patient by using the preset pacing rate, and after a period of time, the self heart rate of the patient is re-evaluated. If the self actual heart rate is above the preset pacing rate (which may be regarded as common heart rate) and lasts for a given duration, for example, 50 bpm or 60 bpm, it indicates that the pacing to the patient at the current pacing rate is effective, so that the patient recovers the self heart rate and is out of a life-critical situation. At this time, the pacing operation on the patient may be terminated. By terminating the pacing to the patient in time, the effect of minimizing the pain to the patient can be achieved.

If the self actual heart rates are below or only a few heart rates are above the first preset pacing heart rate, that is, the common heart rate (50 bpm to 60 bpm, which can be adjusted by the doctor), it indicates that the patient's heart rate has not increased/recovered at the current pacing rate or the increase/recovery is not enough to support proper blood circulation. At this time, the patient's life safety is further ensured by continuing to perform pacing to the patient.

It is certain that the above values may be preset or adjusted according to the doctor's clinical judgment, so as to adapt to different patients and meet the needs of different patients, further improving the use experience of the user.

It should be noted that all parameter values of the present embodiment may be reset according to actual conditions.

In the present embodiment, for the patient in the life-critical state where the heart rate is severely too slow or even cardiac arrest occurs, by presetting the trigger conditions for the pacing operation, pacing is performed on the patient by using a higher pacing rate only when the pacing is necessary, and the effect of timely and effective pacing is achieved to support the life of the patient, and pacing is terminated when the self heart rate of the patient recovers to a certain level; at the same time, the effect of avoiding, to a great extent, unnecessary pacing for the patient during daily use and the pain of the patient caused by pacing stimulation is also achieved, thereby improving the user's acceptability, compliance and use experience of medical apparatus. In addition, after the pacing operation is implemented, the effectiveness of the pacing operation on the patient is monitored in a timely manner, and the pacing rate is adaptively adjusted to ensure timely and effective ventricular capture, guaranteeing the patient's life safety.

Embodiment 5

A medical device of the present embodiment comprises the pacing control apparatus of Embodiment 3 or 4.

Herein, the medical device includes but is not limited to a wearable cardioverter defibrillator (WCD), an external defibrillator (for example, AED), a subcutaneous implantable cardioverter defibrillator (SICD), a mechanical circulatory support device (MCS), or other life support apparatuses/devices.

Hardware components, circuit structures and the like required for the above pacing control process are all existing structures in the wearable cardioverter defibrillator (WCD), external defibrillator, subcutaneous implantable cardioverter defibrillator (SICD) or mechanical circulatory support device (MCS), that is, how the components work together and how the circuit structures achieve the corresponding functions are well established in the art and therefore will not be repeated here.

The medical device of the present embodiment adopts the above pacing control apparatus, mainly for the patient in the life-critical state where the heart rate is severely too slow or even cardiac arrest occurs. When the patient's heart rate continues to be below the very low preset low heart rate for a period of time, it is determined that the patient needs pacing and it is necessary to perform pacing to the patient, so pacing is performed on the patient by using a higher pacing rate, and the effect of timely and effective pacing is achieved to support the life of the patient: at the same time, the effect of avoiding, to a great extent, unnecessary pacing for the patient during daily use and the pain of the patient caused by pacing stimulation is also achieved, and especially pacing to occasional bradycardia, non-severe bradycardia, or transient arrest cannot be triggered, thereby improving the user's acceptability, compliance and use experience of medical apparatus.

Although the specific embodiments of the present disclosure have been described above, it should be understood by those skilled in the art that these are merely illustrative examples and that a variety of changes or modifications can be made to these embodiments without departing from the principles and essence of the present disclosure. Therefore, the scope of protection of the present disclosure is limited by the appended claims.

What is claimed is:

1. A pacing control method, comprising: obtaining an actual heart rate of a patient; determining whether the actual heart rate meets a preset low heart rate condition, and if so, performing cardiac pacing to the patient by using a preset pacing rate; wherein the preset low heart rate condition is used for representing that the patient is in a life-critical state, and wherein the step of determining whether the actual heart rate meets the preset low heart rate condition, and if so, performing cardiac pacing to the patient by using the preset pacing rate comprises: determining whether the actual heart rate is below the preset low heart rate, if so, obtaining a first low heart rate duration in which the actual heart rate of the patient is consecutively below the preset low heart rate, and when the first low heart rate duration reaches a preset low heart rate duration, performing cardiac pacing to the patient by using the preset pacing rate;
   wherein the preset low heart rate duration ranges from 2 s to 5 min; or, the preset low heart rate duration ranges from 10 s to 60 s.

2. The pacing control method according to claim 1, wherein the preset pacing rate, the preset low heart rate and the preset low heart rate duration are parameters that can be reset according to the patient's condition.

3. The pacing control method according to claim 1 wherein the preset low heart rate is above 0 bpm and below or equal to 40 bpm; or, the preset low heart rate is above or equal to 10 bpm and below or equal to 30 bpm.

4. The pacing control method according to claim 1, wherein the preset pacing rate ranges from 40 bpm to 80 bpm.

5. The pacing control method according to claim 1, wherein during execution of the step of performing cardiac pacing to the patient by using the preset pacing rate, the following steps are executed simultaneously:
   obtaining the number of self heartbeats of the patient during a first pacing time period;
   obtaining the total number of heartbeats of the patient during a given time period;
   wherein the total number of heartbeats comprises the number of self heartbeats and number of pacing heartbeats; and
   the given time period comprises the first pacing time period, and a duration corresponding to the given time period is above or equal to a duration corresponding to the first pacing time period;
   calculating a first ratio of the number of self heartbeats to the total number of heartbeats;
   determining whether the first ratio is above or equal to a first given threshold, and if the first ratio is above or equal to the first given threshold, controlling to terminate pacing; if the first ratio is below the first given threshold, determining whether the first ratio is below or equal to a second given threshold, if the first ratio is below or equal to the second given threshold, continuing to execute the step of performing cardiac pacing to the patient by using the preset pacing rate; if the first ratio is above the second given threshold and below the first given threshold, reducing the preset pacing rate to a first pacing rate, and determining whether the first pacing rate is below a minimum pacing rate, if not, performing cardiac pacing to the patient by using the first pacing rate; and if so, performing cardiac pacing to the patient by using the minimum pacing rate.

6. The pacing control method according to claim 5, wherein the first given threshold ranges from 50% to 100%, the second given threshold ranges from 0 to 30%, and the minimum pacing rate ranges from 40 bpm to 60 bpm.

7. The pacing control method according to claim 1, wherein the pacing control method also comprises:
   obtaining the number of pacing heartbeats of the patient during a first pacing time period;
   obtaining the total number of heartbeats of the patient during a given time period;
   wherein the total number of heartbeats comprises the number of self heartbeats and the number of pacing heartbeats;
   the given time period comprises the first pacing time period, and a duration corresponding to the given time period is above or equal to a duration corresponding to the first pacing time period;
   calculating a second ratio of the number of pacing heartbeats to the total number of heartbeats;
   determining whether the second ratio is below or equal to a third given threshold, and if the second ratio is below or equal to the third given threshold, controlling to terminate pacing; if the second ratio is above the third given threshold, determining whether the second ratio is above or equal to a fourth given threshold, if the second ratio is above or equal to the fourth given threshold, continuing to execute the step of performing cardiac pacing to the patient by using the preset pacing rate; if the second ratio is below the fourth given threshold and above the third given threshold, reducing the preset pacing rate to a first pacing rate; and determining whether the first pacing rate is below a minimum pacing rate, if not, performing cardiac pacing to the patient by using the first pacing rate; and if so, performing cardiac pacing to the patient by using the minimum pacing rate.

8. The pacing control method according to claim 7, wherein the third given threshold ranges from 0 to 50%, the fourth given threshold ranges from 0 to 100%, and minimum pacing rate ranges from 40 bpm to 60 bpm.

9. A pacing control apparatus, comprising: a heart rate acquisition module for obtaining an actual heart rate of a patient; a first determination module for determining whether the actual heart rate meets a preset low heart rate condition, and if so, calling a pacing module to perform cardiac pacing to the patient by using a preset pacing rate; wherein the preset low heart rate condition is used for representing that the patient is in a life-critical state, and wherein the first determination module is used for determining whether the actual heart rate is below the preset low heart rate, if so, obtaining a first low heart rate duration in which the actual heart rate of the patient is consecutively below the preset low heart rate, and the first determination module is also used for calling the pacing module to perform cardiac pacing to the patient by using the preset pacing rate when the first low heart rate duration reaches a preset low heart rate duration;
   wherein the preset low heart rate duration ranges from 2 s to 5 min; or, the preset low heart rate duration ranges from 10 s to 60 s.

10. The pacing control apparatus according to claim 9, wherein the preset pacing rate, the preset low heart rate and the preset low heart rate duration are parameters that can be reset according to the patient's condition.

11. The pacing control apparatus according to claim 9, wherein the preset low heart rate is above 0 bpm and below or equal to 40 bpm; or, the preset low heart rate is above or equal to 10 bpm and below or equal to 30 bpm.

12. The pacing control apparatus according to claim 9, wherein the preset pacing rate ranges from 40 bpm to 80 bpm.

13. The pacing control apparatus according to claim 9, wherein the pacing control apparatus also comprises:

a self-heartbeat number acquisition module for obtaining the number of self heartbeats of the patient during a first pacing time period;

a total-heartbeat number acquisition module for obtaining the total number of heartbeats of the patient during a given time period;

wherein the given time period comprises the first pacing time period, and a duration corresponding to the given time period is above or equal to a duration corresponding to the first pacing time period;

a first ratio calculation module for calculating a first ratio of the number of self heartbeats to the total number of heartbeats;

a second determination module for determining whether the first ratio is above or equal to a first given threshold, and if the first ratio is above or equal to the first given threshold, controlling to terminate pacing; if the first ratio is below the first given threshold, determining whether the first ratio is below or equal to a second given threshold, if the first ratio is below or equal to the second given threshold, calling the pacing module to perform cardiac pacing to the patient by using the preset pacing rate; if the first ratio is above the second given threshold and below the first given threshold, calling the pacing module to reduce the preset pacing rate to a first pacing rate, and determining whether the first pacing rate is below a minimum pacing rate, if not, performing cardiac pacing to the patient by using the first pacing rate; and if so, performing cardiac pacing to the patient by using the minimum pacing rate.

14. The pacing control apparatus according to claim 13, wherein the first given threshold ranges from 50 to 100%, the second given threshold ranges from 0 to 30%, and the minimum pacing rate ranges from 40 bpm to 60 bpm.

15. The pacing control apparatus according to claim 9, wherein the pacing control apparatus also comprises:

a pacing-heartbeat number acquisition module for obtaining the number of pacing heartbeats of the patient during a first pacing time period;

a total-heartbeat number acquisition module for obtaining the total number of heartbeats of the patient during a given time period; wherein the total number of heartbeats comprises number of self heartbeats and the number of pacing heartbeats; and the given time period comprises the first pacing time period, and a duration corresponding to the given time period is above or equal to a duration corresponding to the first pacing time period;

a second ratio calculation module for calculating a second ratio of the number of pacing heartbeats to the total number of heartbeats;

a third determination module for determining whether the second ratio is below or equal to a third given threshold, if the second ratio is below or equal to the third given threshold, controlling to terminate pacing; if the second ratio is above the third given threshold, determining whether the second ratio is above or equal to a fourth given threshold, if the second ratio is above or equal to the fourth given threshold, calling the pacing module to continue to perform cardiac pacing to the patient by using a preset pacing rate; if the second ratio is below the fourth given threshold and above the third given threshold, calling the pacing module to reduce the preset pacing rate to a first pacing rate, and determining whether the first pacing rate is below a minimum pacing rate, if not, performing cardiac pacing to the patient by using the first pacing rate; and if so, performing cardiac pacing to the patient by using the minimum pacing frequency-rate.

16. The pacing control apparatus according to claim 14, wherein the third given threshold ranges from 0 to 50%, the fourth given threshold ranges from 70 to 100%, and minimum pacing rate ranges from 40 bpm to 60 bpm.

17. A medical device, comprising the pacing control apparatus according to claim 9.

18. The medical device according to claim 17, wherein the medical device comprises a wearable cardioverter defibrillator (WCD), an external defibrillator, a subcutaneous implantable cardioverter defibrillator (SICD), or a mechanical circulatory support device (MCS).

* * * * *